(12) United States Patent
Bar-Tal et al.

(10) Patent No.: US 10,856,771 B2
(45) Date of Patent: Dec. 8, 2020

(54) ABLATION SIZE ESTIMATION AND VISUAL REPRESENTATION

(71) Applicant: Biosense Webster (Israel) Ltd., Yokneam (IL)

(72) Inventors: Meir Bar-Tal, Haifa (IL); Aharon Turgeman, Zichron Ya'acov (IL)

(73) Assignee: Biosense Webster (Israel) Ltd., Yokneam (IL)

(*) Notice: Subject to any disclaimer, the term of this patent is extended or adjusted under 35 U.S.C. 154(b) by 628 days.

(21) Appl. No.: 15/721,042

(22) Filed: Sep. 29, 2017

(65) Prior Publication Data

US 2019/0099112 A1 Apr. 4, 2019

(51) Int. Cl.
*A61B 18/12* (2006.01)
*A61B 5/107* (2006.01)
*A61B 18/14* (2006.01)
*A61B 5/00* (2006.01)
*A61B 5/06* (2006.01)
(Continued)

(52) U.S. Cl.
CPC .............. *A61B 5/107* (2013.01); *A61B 5/065* (2013.01); *A61B 5/6852* (2013.01); *A61B 5/742* (2013.01); *A61B 18/1492* (2013.01); *A61B 18/08* (2013.01); *A61B 2018/00577* (2013.01); *A61B 2034/104* (2016.02); *A61B 2034/2051* (2016.02)

(58) Field of Classification Search
CPC ......... A61B 5/107; A61B 5/066; A61B 5/742; A61B 5/7425; A61B 5/6852; A61B 5/065; A61B 18/1492; A61B 18/08; A61B 18/14; A61B 18/1206; A61B 18/1233; A61B 2018/00577; A61B 2018/00988; A61B 2034/2051; A61B 2034/104

USPC ......... 600/374; 604/22, 113; 606/32–34, 38, 606/41, 42; 607/98–101, 113, 115, 116, 607/122

See application file for complete search history.

(56) References Cited

U.S. PATENT DOCUMENTS 5,391,199 A 2/1995 Ben-Haim
5,443,489 A 8/1995 Ben-Haim
(Continued)

FOREIGN PATENT DOCUMENTS

WO 2017/160808 A1 9/2017

OTHER PUBLICATIONS

Extended European Search Report dated Feb. 19, 2019 for the European Patent Application No. 18197471.8.

*Primary Examiner* — Thomas A Giuliani

(57) ABSTRACT

A system for visually representing estimated ablation size is provided which includes sensors that acquire location signals indicating locations of an ablation device during an ablation of an organ and ablation parameters signals indicating ablation parameters during the ablation. The system also includes memory which stores location data and ablation parameter data corresponding to the location signals and ablation parameters signals. The system also includes a processing device which generates mapping information for displaying a map of the organ and first object information for displaying a first geometrical object having a first size which represents an estimated depth of the ablation of the organ. The processing device also generates second object information for displaying, concurrently with the first geometrical object, a second geometrical object having a second size which represents an estimated width of the ablation of the organ.

13 Claims, 5 Drawing Sheets

(51) Int. Cl.
    *A61B 34/20*     (2016.01)
    *A61B 34/10*     (2016.01)
    *A61B 18/08*     (2006.01)
    *A61B 18/00*     (2006.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |
| 6,456,828 B1 | 9/2002 | Ozluturk |
| 6,690,963 B2 | 2/2004 | Ben-Haim |
| 6,788,967 B2 | 9/2004 | Ben-Haim |
| 2003/0199755 A1 | 10/2003 | Halperin et al. |
| 2008/0071173 A1 | 3/2008 | Aldrich |
| 2009/0093806 A1 | 4/2009 | Govari et al. |
| 2009/0138007 A1 | 5/2009 | Govari et al. |
| 2011/0046483 A1 | 2/2011 | Fuchs et al. |
| 2015/0335344 A1 | 11/2015 | Aljuri et al. |
| 2016/0117857 A1* | 4/2016 | State .................. G06T 15/20 345/420 |

* cited by examiner

ABLATION SIZE ESTIMATION AND VISUAL REPRESENTATION

SUMMARY

The present application discloses a system for visually representing estimated ablation size. The system includes sensors configured to acquire: location signals indicating locations of an ablation device during an ablation of an organ; and ablation parameter signals indicating ablation parameters during the ablation. The system also includes memory configured to store: location data corresponding to the location signals; and ablation parameter data corresponding to the ablation parameter signal. The system also includes a processing device configured to generate, from the location data, mapping information for displaying a map of the organ. The processing device is also configured to generate, from the ablation parameter data, first object information for displaying a first geometrical object having a first size which represents an estimated depth of the ablation of the organ. The processing device is also configured to generate, from the ablation parameter data, second object information for displaying, concurrently with the first geometrical object, a second geometrical object having a second size which represents an estimated width of the ablation of the organ.

The present application discloses a method of visually representing ablation size. The method includes receiving location data corresponding to location signals indicating locations of an ablation device during an ablation of an organ and receiving ablation parameter data corresponding to ablation parameter signals indicating ablation parameters during the ablation. The method also includes generating, from the location data, mapping information for displaying a map of the organ. The method also includes generating, from the ablation parameter data, first object information for displaying a first geometrical object having a first size which represents an estimated depth of the ablation of the organ. The method further includes generating, from the ablation parameter data, second object information for displaying, concurrently with the first geometrical object, a second geometrical object having a second size which represents an estimated width of the ablation of the organ.

The present application discloses a non-transitory computer readable medium having instructions for causing a computer to perform a method which includes receiving location data corresponding to location signals indicating locations of an ablation device during an ablation of an organ and receiving ablation parameter data corresponding to ablation parameter signals indicating ablation parameters during the ablation. The method also includes generating, from the location data, mapping information for displaying a map of the organ and generating, from the ablation parameter data, first object information for displaying a first geometrical object having a first size which represents an estimated depth of the ablation of the organ. The method further include generating, from the ablation parameter data, second object information for displaying, concurrently with the first geometrical object, a second geometrical object having a second size which represents an estimated width of the ablation of the organ.

BRIEF DESCRIPTION OF THE DRAWINGS

A more detailed understanding can be had from the following description, given by way of example in conjunction with the accompanying drawings wherein.

DETAILED DESCRIPTION

Conventional ablation methods and systems, such as radio-frequency (RF) catheter ablation, are used to ablate portions of dysfunctional tissue, such as tissue of a heart, lung, ear, nose, throat or other organs. For example, an RF catheter ablation procedure typically includes inserting a catheter through an incision in the skin and guiding the catheter to an organ where the catheter is used to create ablation lesions on the organ tissue.

Dynamic maps of the patient anatomy (e.g., organs) are created to facilitate accurate determination of regions for ablation. Target ablation sites (i.e., regions of interest (ROI)) of an organ are identified by viewing the maps. Based on the identified ablation sites, an ablation procedure, which includes one or more ablations, is performed on the organ. The conventional methods and systems used to identify these ablation sites and perform the ablation procedure are time consuming (e.g., several hours) and rely on medical personnel with specific expertise and experience (typically requiring many hours of training).

Successful treatment depends on accurate identification of ablation sites as well as an accurate assessment of the ablations performed on the organ. Some conventional systems attempt to provide an accurate assessment of the ablations by displaying ablation parameters (e.g., ablation time, catheter position stability, ablation power, temperature, and ablation impedance) to a user (e.g., physician). For example, numerical values for the ablation parameters are displayed. Different colors are also displayed on the maps to indicate the values of different ablation parameters.

Accurate and consistent ablation results are also facilitated by accurate and efficient visualization of ablation size (i.e., depth and width). While conventional systems provide some indication regarding ablation size, an improved system and method is needed to facilitate an accurate and efficient visualization of ablation size.

Embodiments disclosed herein employ systems, apparatuses and methods of providing a visual representation of estimated ablation depths and widths to facilitate an accurate and efficient visualization of ablation sizes. Embodiments include displaying a first geometrical object to visually represent a depth of an ablation and displaying, concurrently with the first geometrical object, a second geometrical object to visually represent a width of the ablation.

Figure 1:
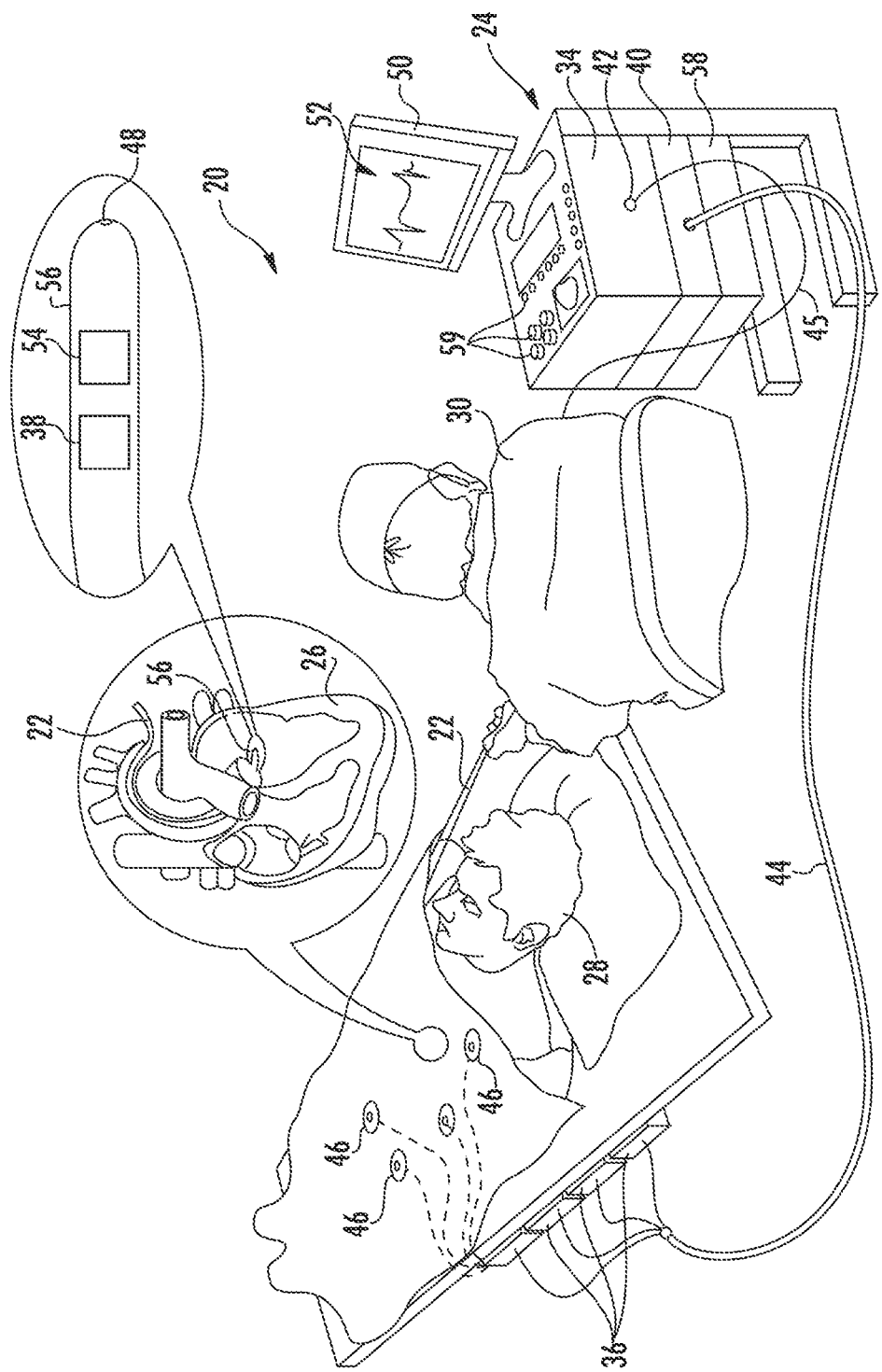
FIG. 1 is an illustration of an example medical system for navigating a tool in three dimensional (3-D) space according to embodiments disclosed herein.

Referring now to FIG. 1, an illustration of an example medical system 20 is shown that may be used to generate and display information 52 (e.g., anatomical models of a portion of a patient and signal information). Tools such as tool 22, can be any tool used for diagnostic or therapeutic treatment, such as for example, a catheter (such as catheter 202 shown in FIG. 2 and described in more detail below)

configured to ablate portions of patient anatomy as well as mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The operator 30 may also advance the tool so that the tip 56 engages endocardial tissue at one or more locations. The control console 24 may include an RF generator, such as RF generator 218 shown in FIG. 2, which supplies high-frequency electrical energy via the tool 22 for ablating tissue at locations engaged by the tip 56.

The control console 24 may also use magnetic position sensing to determine three-dimensional (3-D) position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 1 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The tool 22 may also include a force sensor 54 disposed at the tip 56 of tool 22. The force sensor 54 may measure a force applied by the tool 22 (e.g., the tip 56 of the tool 22) to the endocardial tissue of the heart 26 and generate a signal that is sent to the control console 24. The force sensor 54 may include a magnetic field transmitter and a receiver connected by a spring (not shown), and may generate an indication of the force based on measuring a deflection of the spring. Further details of this sort of probe and force sensor are described in U.S. Patent Application Publications 2009/0093806 and 2009/0138007, whose disclosures are incorporated herein by reference. Alternatively, the tool 22 may include another type of force sensor that may use, for example, fiber optics or impedance measurements.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in an organ, such as the heart 26 shown in FIG. 1.

Although the example medical system 20 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on acquired location signals (e.g., the electrical impulses received from the body surface electrodes 46 and the electrical signals received from the tool 22 via the I/O interface 42 and other components of medical system 20), the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit enabling local digital signal processing, a radio link, and a miniaturized rechargeable battery.

In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 may assist in providing a location of the tool (e.g., catheter) in 3-D space by detecting electrical impulses (e.g., generated by the polarization and depolarization of cardiac tissue and transmitting information to the control console 24, via the cable 44). The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is an example. Any suitable configuration of the medical system 20 may be used and implemented.

Figure 2:
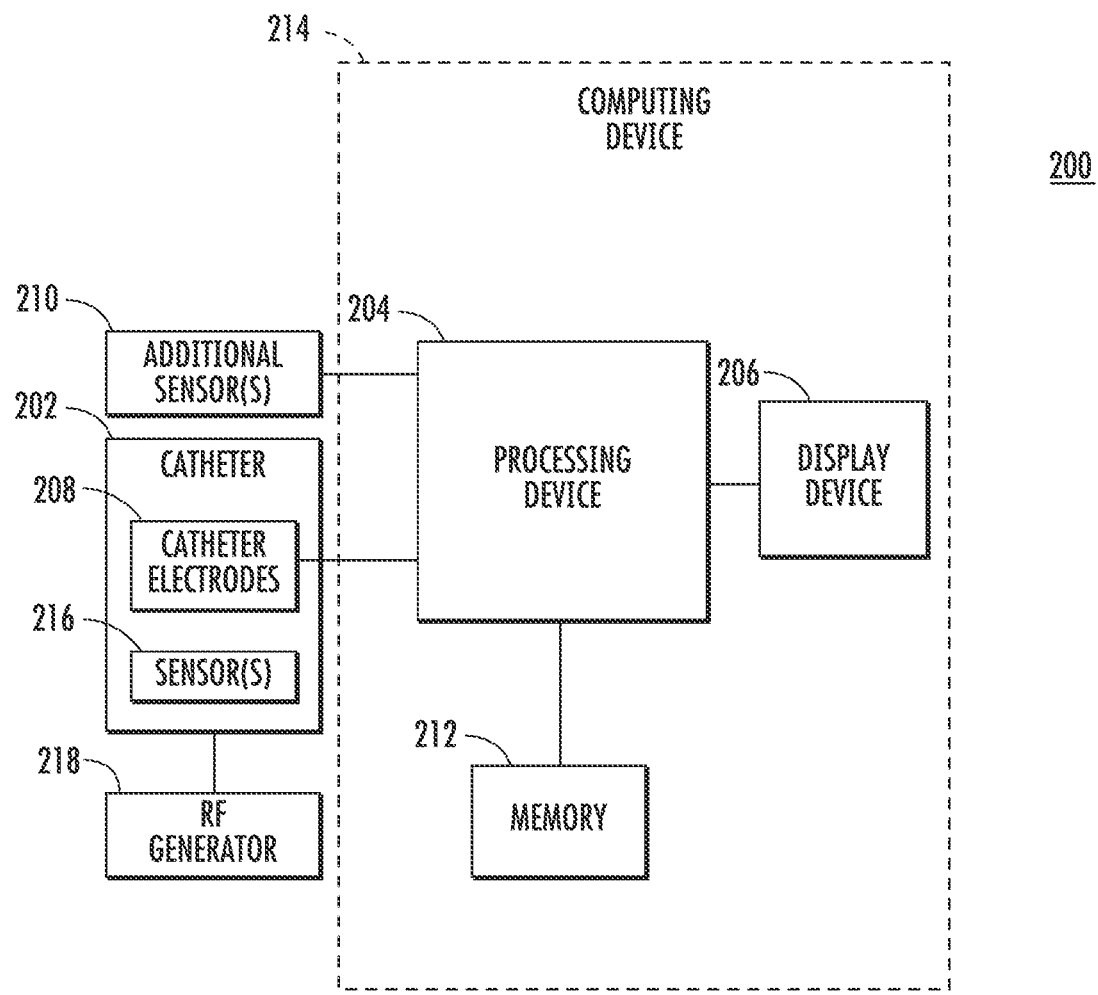
FIG. 2 is an illustration of components of an example medical system for use with embodiments described herein.

FIG. 2 is a block diagram illustrating example components of a medical system 200 for use with embodiments described herein. As shown in FIG. 2, the system 200 includes a catheter 202, a processing device 204, a display device 206, memory 212 and RF generator 218, which supplies high-frequency electrical energy, via catheter 202, for ablating tissue at locations engaged by the catheter 202. As shown in FIG. 2, the processing device 204, display device 206 and memory 212 are a part of computing device 214. In some embodiments, the display device 206 may be separate from computing device 214. Computing device 214 may also include an I/O interface, such as I/O interface 42 shown in FIG. 1.

For explanation purposes, a single ablation device (e.g., catheter 202) is described herein as performing a mapping procedure and an ablation procedure. Different types of ablation devices (e.g., different types of catheters) may, however, be used to perform mapping procedures and ablation procedures.

As shown in FIG. 2, the example catheter 202 includes one or more sensors 216, which include, for example, a magnetic field location sensor (e.g., sensor 38 in FIG. 1) for providing location signals to indicate the 3-D position coordinates of the catheter 202. In some procedures, one or more additional sensors 210 that are separate from the catheter 202, as shown in example system 200, are also used to provide location signals. In some embodiments, the catheter 202 also includes catheter electrodes 208 for mapping electrical potentials of a heart.

Sensor(s) 216 also include, for example, position sensors, pressure or force sensors, temperature sensors, impedance sensors or other sensors which provide ablation parameter signals indicating ablation parameters during the ablation of tissue of an organ. During the ablation procedure, RF generator 218 supplies high-frequency electrical energy, via catheter 202, for ablating tissue at locations engaged by the catheter 202. Sensor(s) 216 sense ablation parameters (e.g., catheter position stability, temperature, ablation time, ablation power and ablation impedance) during the ablation procedure. Catheter 202 may be in wired or wireless communication with processing device 204 to communicate the information acquired by sensor(s) 216.

The location signals are processed as location data and stored, for example, in memory 212. The processing device 204 receives (e.g., reads from memory) location data corresponding to the location signals and generates mapping information, from the location data, for displaying one or more maps of an organ being ablated. The ablation parameter signals are processed as ablation parameter data and stored, for example, in memory 212.

The processing device 204 receives the ablation parameter data corresponding to the ablation parameter signals and generates, from the ablation parameter data, first object information for displaying a first geometrical object having a first size which represents an estimated depth of the ablation of the organ. Processing device 204 also receives, from the ablation parameter data, second object information for displaying, concurrently with the first geometrical object, a second geometrical object having a second size which represents an estimated width of the ablation of the organ.

That is, the processing device 204 receives the ablation parameter data corresponding to ablation parameter signals acquired (e.g., via one or more sensors 216) during the ablation procedure, determines from the ablation parameter data, estimated depth and width of an ablation, and generates, from the ablation parameter data, object information for displaying geometric objects to visually represent the estimated ablation depth and width. For example, using the ablation parameter data, processing device 204 executes a plurality of programmed instructions (e.g., lesion estimation and assessment algorithms) to determine an estimated depth and width of an ablation. The processing device 204 then generates first object information for displaying a first geometrical object having a first size which represents the estimated depth for an ablation of the heart. The processing device 204 also generates second object information for displaying, concurrently with the first geometrical object, a second geometrical object having a second size which represents the estimated width for the ablation of the heart.

The processing device 204 may also use the ablation parameter data to execute the programmed instructions to generate in-blood information for displaying an indicator on the map of an organ to visually represent a portion of the organ tissue which was not contacted during the ablation procedure. For example, during the ablation procedure, ablation parameter signals may be acquired, via sensor(s) 216, indicating whether the catheter 202 contacts the organ tissue at a portion of the heart. The ablation parameter signals may include, for example, information identifying the location of the catheter in 3-D space at a particular time, information identifying a force applied by the catheter, impedance information and other information indicating whether the catheter 202 contacts the organ tissue at the portion of the organ.

The processing device 204 processes the ablation parameter signals as ablation parameter data and uses the ablation parameter data to determine whether the catheter 202 contacted the organ tissue at the portion of the organ. If no contact is determined between the ablation device and the heart tissue at the portion of the organ, the processing device 204 generates in-blood indicator information, indicating an in-blood ablation (as opposed to an ablation of the organ tissue).

Processing device 204 drives display device 206, using the mapping information, to display the map of the organ on display device 206. Processing device 204 also drives display device 206, using the the first object information and the second object information, to display the first and second geometrical objects at the display device 206 as well as any determined in-blood indicators.

Display device 206 may include one or more displays each configured to display one or more maps of the organ. For example, display device 206 is configured to display maps representing a spatio-temporal manifestation of an organ (e.g., a heart) as well as geometrical objects which represent estimated ablation depths and widths. Display device 206 may be in wired or wireless communication with processing device 204. In some embodiments, display device may be separate from computing device 214.

Memory 212 includes, for example, volatile and non-volatile memory, such as random access memory (RAM), dynamic RAM, or a cache. Memory 212 also includes, for example, storage 214, such as, fixed storage (e.g., a hard disk drive and a solid state drive) and removable storage (e.g., an optical disk and a flash drive).

Figure 3:
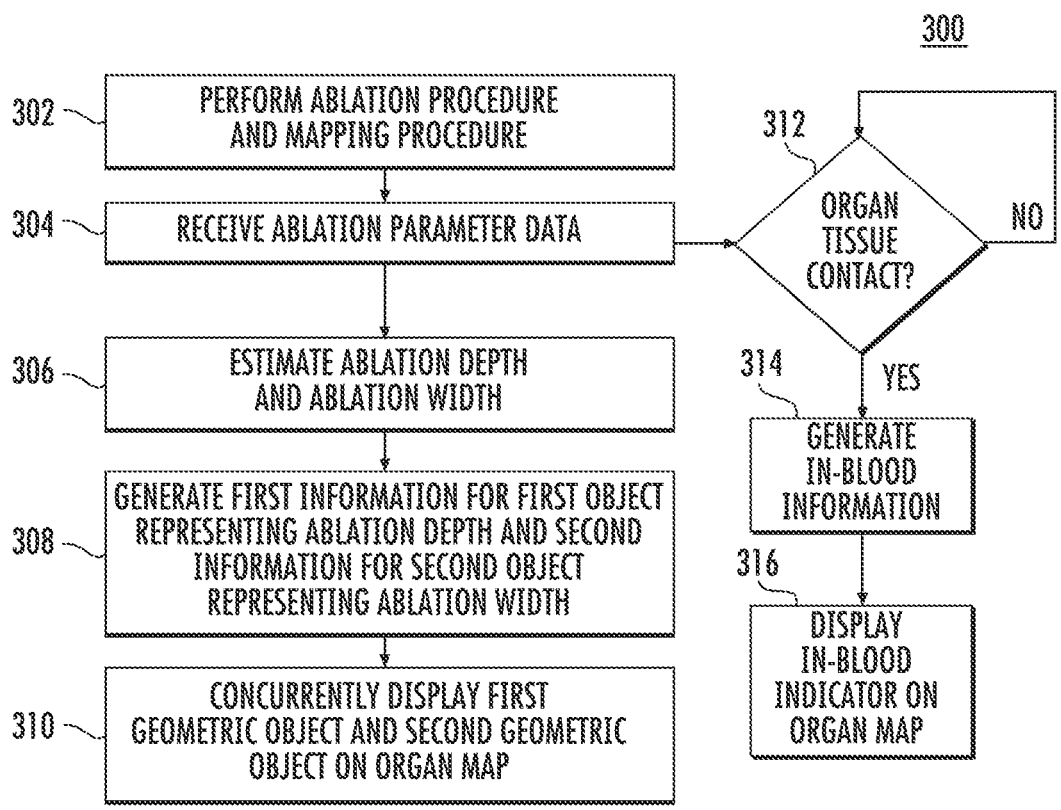
FIG. 3 is a flow diagram illustrating an example method of providing a visual representation of ablation width and ablation depth.

FIG. 3 is a flow diagram illustrating an exemplary method 300 of visually representing an estimated ablation size. As shown at block 302, the method includes performing an ablation procedure and a mapping procedure. For example, during the ablation of an organ, location data, corresponding to location signals indicating locations of an ablation device during an ablation of an organ. Based on the location data, mapping information is generated (e.g., via processing device 204). As part of the mapping procedure, one or more maps of an organ (e.g., map of a heart) are displayed (e.g., at display device 206) according to the mapping information. The mapping information can be provided to the display via a wired medium or wirelessly via a network.

As shown at block 304, the method 300 includes receiving ablation data corresponding to ablation parameters acquired during the ablation procedure. For example, one or more ablations of organ tissue are performed as part of the ablation procedure. For each ablation performed during the ablation procedure, system parameter signals are acquired (e.g., via sensor(s) 216). The system parameter signals are processed as ablation parameter data (e.g., via signal processor 40) and stored (e.g., in memory 212).

As shown at block 306, the method 300 includes estimating an ablation depth and an ablation width. For example, using ablation parameter data corresponding to acquired ablation parameter signals, depth and width of an ablation is estimated according to lesion assessment algorithms.

As shown at block 308, the method 300 includes generating, from the ablation parameter data, first object information for displaying a first geometrical object having a first size which visually represents an estimated depth of an ablation of the organ and second object information for displaying, concurrently with the first geometrical object, a second geometrical object having a second size which visually represents an estimated width of the ablation of the organ. For example, using the ablation depth estimated from the ablation parameter data at block 308, first object information is generated for displaying a first geometrical object having a first size which represents an estimated depth of an ablation of the organ. In addition, second object information is generated for displaying a second geometrical object having a second size which represents an estimated width of the ablation of the organ.

As shown at block 310, the method 300 includes visually displaying (e.g., at display device 206) the first geometrical object and the second geometrical object on the organ map. For simplified explanation purposes, an example of implementing the method 300 is now described with reference to a heart. Embodiments described herein may, however, be used to estimate ablation sizes for ablations performed on other portions of patient anatomy, such as for example, tissue in lungs, ears, noses, throats and other organs.

Figure 4:
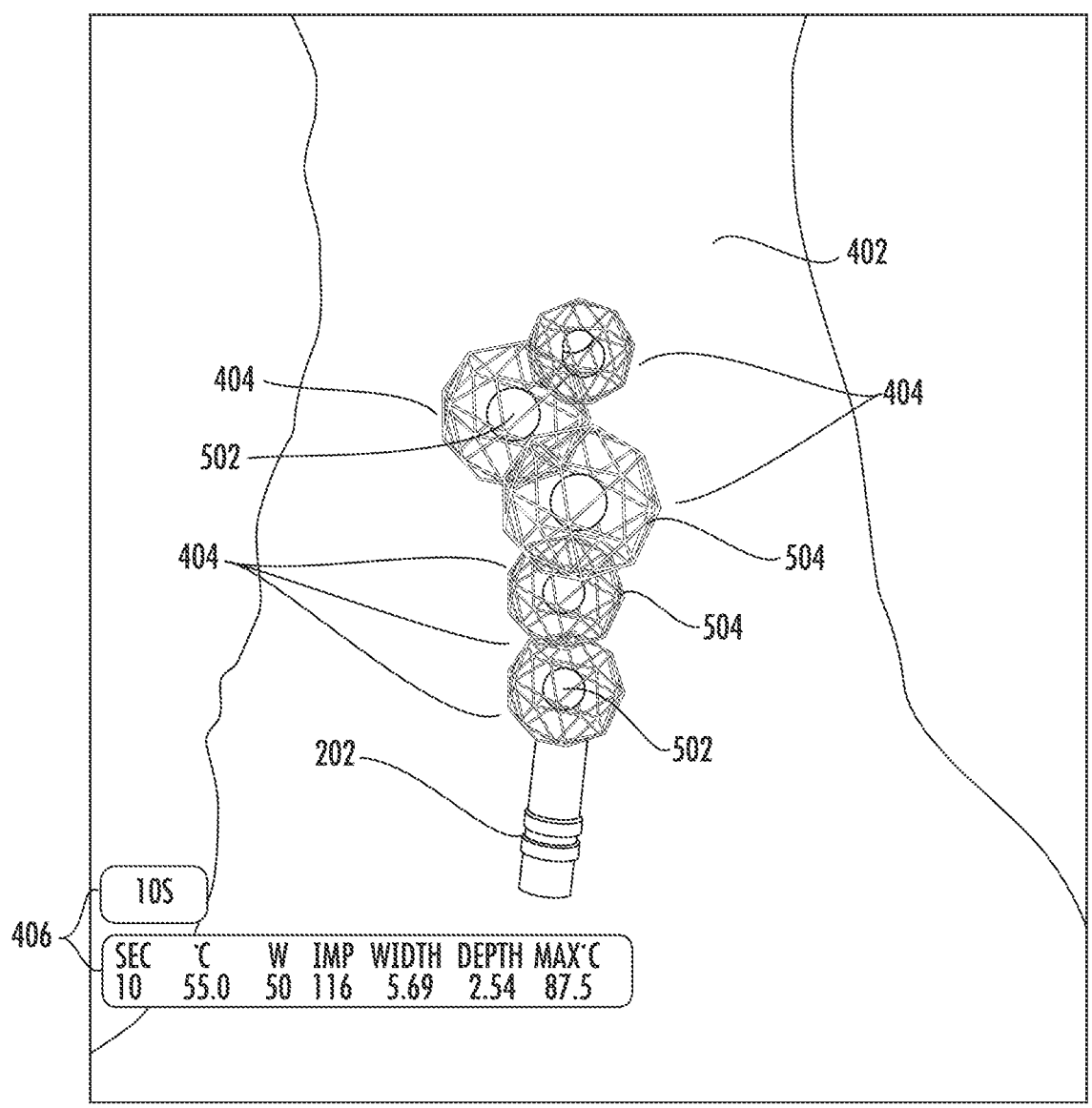
FIG. 4 is an example display of geometric objects representing depths and widths for ablations of a heart according to an embodiment.
Figure 5:
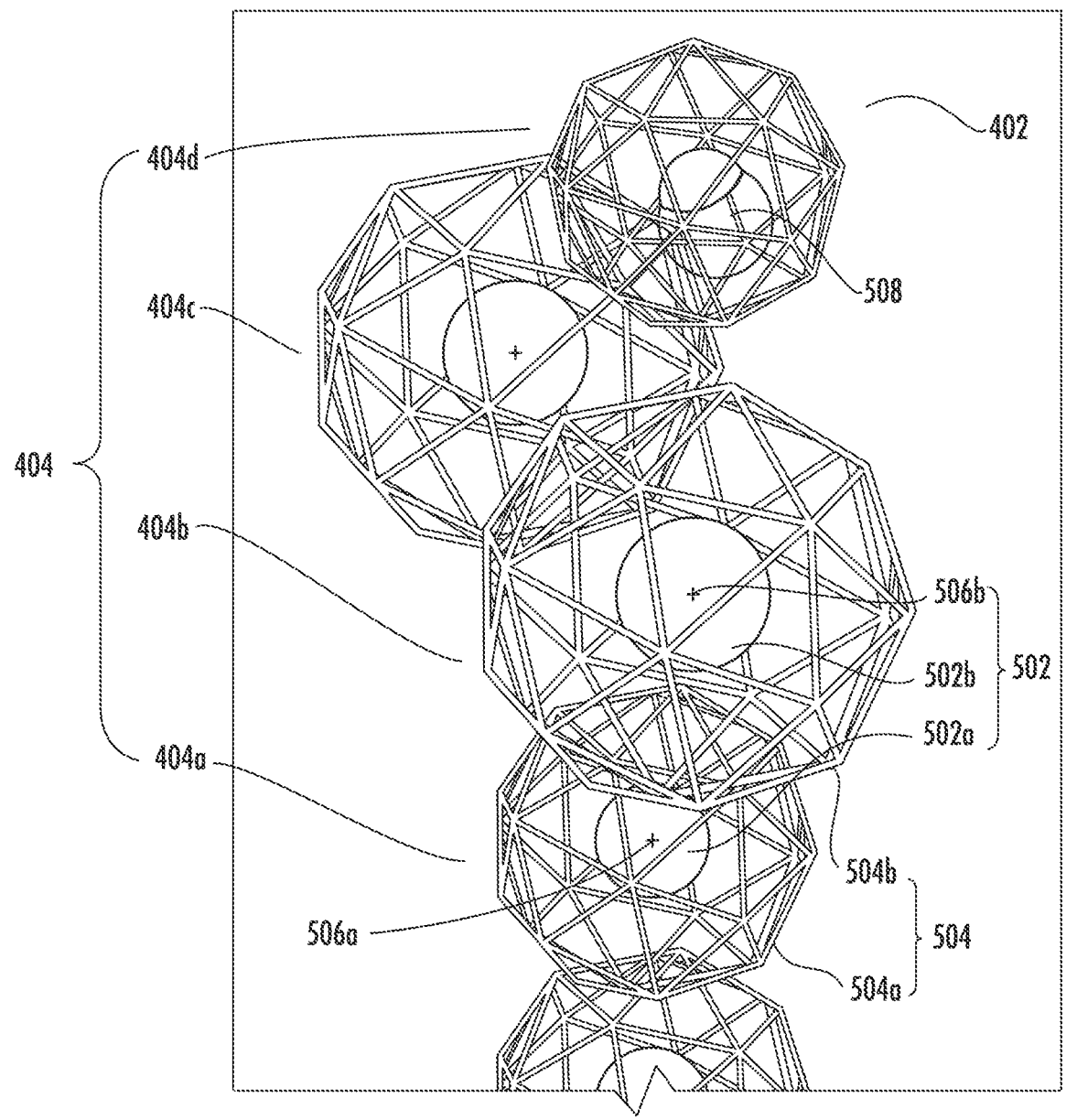
FIG. 5 is a close-up view of the display shown in FIG. 4 illustrating exemplary first and second geometric objects representing ablation depths and widths.

FIG. 4 is an example display 400 of geometric objects 502 and 504 representing depths and widths for ablations 404 of heart 402. FIG. 5 is a close-up view of the display 400 shown in FIG. 4 illustrating the exemplary first geometric objects 502 for representing the ablation depths and second geometric objects 504 for representing the ablation widths of ablations 404a-404d.

A map of a portion of a heart 402 is shown at display 400. The map is generated, for example, from ECG data corresponding to electrical signals acquired via electrodes disclosed on the heart 402. Five separate ablations 404, performed over time at different ablations sites on the heart 402, are shown at display 400. The number and location of the ablations 404 shown in FIG. 4 is merely exemplary. As shown in FIGS. 4 and 5, each ablation 404 is represented by a first geometric object 502 and a second geometric object 504 displayed on the map of the heart 402. As described in more detail below with regard to FIG. 5, first geometric objects 502 are used to visually represent the depth of each ablation 404 and second geometric objects 504 are used to visually represent the width of each ablation 404.

Additional ablation parameter data 406 is also shown at display 400 in FIG. 4. As shown, the ablation parameter data 406 data includes numerical values for different ablation parameter types (e.g., ablation time, temperature, power, impedance width and depth and max temperature). The ablation parameter types shown in FIG. 4 are merely exemplary. Displays may include other ablation parameter types and values for the ablation parameter types. In addition, other ablation parameter data, such as different indicators (e.g., colors) each indicating ablation parameters, may be displayed on the organ. Indicator bars (e.g., color bars) corresponding to the different indicators on the organ may also be displayed.

FIG. 5 shows four ablations 404a-404d of the six ablations 404 shown in FIG. 4. The size of first geometric object 502a represents the depth of ablation 404a and the size of second geometric object 504a represents the width of ablation 404a. The size of first geometric object 502b represents the depth of ablation 404b and the size of second geometric object 504b represents the width of ablation 404b. For simplification purposes, the geometric objects representing the depth and width of ablations 404c and 404d are not specifically annotated in FIG. 5.

While sizes of geometric objects used to represent the depth and width of each ablation may be different, the centers of both geometrics objects are displayed at the same location on a map, corresponding to ablation centers in 3-D space. For example, as shown in FIG. 5, while the size of first geometric object 502a is smaller than the size of the second geometric object 504a, the first geometric object 502a and the second geometric object 504a share the same center 506a, corresponding to the center of the ablation 404a in 3-D space. Likewise, while the size of first geometric object 502b is smaller than the size of the second geometric object 504b, the first geometric object 502b and the second geometric object 504b share the same center 506b, corresponding to the center of the ablation 404b in 3-D space.

The circular shapes of the first geometric objects 502 shown in FIG. 5 are exemplary. Shapes of first geometric objects representing ablation depths may be any geometrical shape. First geometric objects representing ablation depths may be displayed as opaque, transparent or partially transparent. The polygonal shapes of the second geometric objects 502 shown in FIG. 5 are also exemplary. Shapes of second geometric objects representing ablation widths may also be any geometrical shape.

At least a portion of each second geometrical object 504 representing an ablation width is displayed as transparent (or partially transparent) such that both the second geometrical object 504 and the corresponding first geometrical object 502 are simultaneously visible on the map of the heart 402. For example, the second geometric objects 504 shown in FIG. 5 are wire-framed objects. That is, non-wire portions of the wire-framed second geometric objects 504 are transparent such that the first geometrical objects 502 are simultaneously visible on the map of the heart 402. First geometric objects 502 may be displayed as opaque objects. In addition portion of each first geometric object 502 may be displayed as transparent or partially transparent.

As shown in FIGS. 4 and 5, the shapes (e.g., circles) of the first geometrical objects 502 are different from the shapes (e.g., wire framed polyhedrons) of the second geometrical objects 504. For example, the shape of first geometrical object 502a is different from the shape of second geometrical object 504a. The shapes of first and second geometrical objects may, however, also be the same. For example, the shape of a first geometrical object representing the depth of an ablation may be a circle and the second geometrical object representing the width of the ablation may also be a circle (e.g., a wire-framed circle, a semi-transparent circle or other type of circle such that the first geometric object may be also be viewed).

The processing device 204 may also use the ablation parameter data to execute the programmed instructions to generate in-blood indicator information for displaying an indicator on the map of the heart to visually represent a portion of the heart tissue which was not contacted during the ablation procedure. For example, during the ablation procedure, ablation parameter signals may be acquired, via sensor(s) 216, indicating whether an ablation device (e.g., catheter 202) contacted a portion of an organ (e.g., heart tissue at a portion of a heart). The ablation parameter signals may include, for example, information identifying the location of the catheter in 3-D space at a particular time, information identifying a force applied by the catheter, impedance information and other information indicating whether the catheter 202 contacted the portion of the organ.

Referring back to FIG. 3, as shown at decision block 312, the method 300 includes determining whether the ablation device (e.g., catheter 202) contacts a portion of the organ. For example, ablation parameter signals, indicating information (e.g., information identifying the location of the ablation device in 3-D space at a particular time, information identifying a force applied by the ablation device and impedance information) are acquired. Using ablation parameter data, which correspond to the ablation parameter signals, it is determined (e.g., via processing device 204) whether the ablation device contacts the portion of the organ. If no contact is determined, at decision block 312, in-blood indicator information is generated, at block 314, and used to display an indicator on the map of the organ to visually represent the portion of the organ having no contact with the ablation device, as shown at block 316.

For example, as shown in FIG. 5, in-blood indicator 508 is displayed at a location on the map of the heart 402 corresponding to the portion of the heart tissue in 3-D space having no contact with the ablation device. The in-blood indicator 508 is a visual indication that the ablation was an in-blood ablation and not an ablation of the heart tissue. The indicator 508 shown in FIG. 5 is exemplary. Any visual indicator (e.g., color, shading, markings or other visual indicator) can be used to indicate an in-blood ablation. If no contact is determined between the ablation device and the organ at decision block 312, the method proceeds back to decision block 312 to determine whether there is contact between the organ and the ablation device for the next ablation.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A system for visually representing estimated ablation size, the system comprising:
an ablation device configured to perform an ablation procedure using radio-frequency energy to ablate an organ;

sensors configured to acquire: location signals indicating locations of the ablation device during the ablation of the organ; and ablation parameter signals indicating ablation parameters during the ablation;

memory configured to store: location data corresponding to the location signals; and ablation parameter data corresponding to the ablation parameter signals;

a display device;

a processing device configured to:

generate, from the location data, mapping information for displaying a map of the organ;

generate, from the ablation parameter data, first object information for displaying a first geometrical object having a first size which represents an estimated depth of the ablation of the organ;

generate, from the ablation parameter data, second object information for displaying, concurrently with the first geometrical object, a second geometrical object having a second size which represents an estimated width of the ablation of the organ;

display the map of the organ at the display device;

display the first geometrical object and the second geometrical object on the map of the organ at the display device, the first geometrical object having a center and the second geometrical object having a center that is shared with the center of the first geometrical object, wherein the centers of the first geometrical object and the second geometrical object are displayed at the display device at a same location on the map of the organ and correspond to a center of the ablation of the organ;

determine from the ablation parameter data whether the ablation device contacts a portion of the organ;

if no contact is determined between the ablation device and the portion of the organ, generate a visual indicator corresponding to the portion of the organ in three-dimensional space having no contact with the ablation device;

display the visual indicator on the map of the organ.

2. The system of claim 1, wherein at least a portion of the second geometrical object displayed at the display device is transparent such that the first geometrical object and the second geometrical object are both visible on the map of the organ.

3. The system of claim 1, wherein the first geometrical object displayed at the display device is opaque.

4. The system of claim 1, wherein the second geometrical object is wire framed.

5. The system of claim 1, wherein a shape of the first geometrical object is different from a shape of the second geometrical object.

6. The system of claim 1, wherein a shape of the first geometrical object is the same as a shape of the second geometrical object.

7. A computer implemented method of visually representing ablation size, the method comprising:

performing, via an ablation device, an ablation procedure using radio-frequency energy to ablate an organ;

receiving location data corresponding to location signals indicating locations of the ablation device during the ablation of the organ;

receiving ablation parameter data corresponding to ablation parameter signals indicating ablation parameters during the ablation;

generating, from the location data, mapping information for displaying a map of the organ;

generating, from the ablation parameter data, first object information for displaying a first geometrical object having a first size which represents an estimated depth of the ablation of the organ;

generating, from the ablation parameter data, second object information for displaying, concurrently with the first geometrical object, a second geometrical object having a second size which represents an estimated width of the ablation of the organ;

displaying the first geometrical object and the second geometrical object on the map of the organ, wherein the first geometrical object is displayed as having a center and the second geometrical object is displayed as having a center that is shared with the center of the first geometrical object, wherein the centers of the first geometrical object and the second geometrical object are displayed at a same location on the map of the organ and correspond to a center of the ablation of the organ;

determining from the ablation parameter data whether the ablation device contacts a portion of the organ;

if no contact is determined between the ablation device and the portion of the organ, generating a visual indicator corresponding to the portion of the organ in three-dimensional space having no contact with the ablation device; and, displaying the visual indicator on the map of the organ.

8. The method of claim 7, wherein at least a portion of the second geometrical object is transparent such that the first geometrical object and the second geometrical object are both visible on the map of the organ.

9. The method of claim 7, wherein the first geometrical object is opaque.

10. The method of claim 7, wherein the second geometrical object is wire framed.

11. The method of claim 7, wherein a shape of the first geometrical object is different from a shape of the second geometrical object.

12. The method of claim 7, wherein a shape of the first geometrical object is the same as a shape of the second geometrical object.

13. A non-transitory computer readable medium having instructions which cause a computer to perform a method comprising:

receiving location data corresponding to location signals indicating locations of an ablation device during an ablation of an organ;

receiving ablation parameter data corresponding to ablation parameter signals indicating ablation parameters during the ablation;

generating, from the location data, mapping information for displaying a map of the organ;

generating, from the ablation parameter data, first object information for displaying a first geometrical object having a first size which represents an estimated depth of the ablation of the organ;

generating, from the ablation parameter data, second object information for displaying, concurrently with the first geometrical object, a second geometrical object having a second size which represents an estimated width of the ablation of the organ;

displaying the first geometrical object and the second geometrical object on the map of the organ, wherein the first geometrical object is displayed as having a center and the second geometrical object is displayed as having a center that is shared with the center of the first geometrical object, wherein the centers of the first geometrical object and the second geometrical object are displayed at a same location on the map of the organ and correspond to a center of the ablation of the organ;

determining from the ablation parameter data whether the ablation device contacts a portion of the organ;

if no contact is determined between the ablation device and the portion of the organ, generating a visual indicator corresponding to the portion of the organ in three-dimensional space having no contact with the ablation device; and, displaying the visual indicator on the map of the organ.

* * * * *

UNITED STATES PATENT AND TRADEMARK OFFICE
CERTIFICATE OF CORRECTION

| | |
|---|---|
| PATENT NO. | : 10,856,771 B2 |
| APPLICATION NO. | : 15/721042 |
| DATED | : December 8, 2020 |
| INVENTOR(S) | : Meir Bar-Tal et al. |

It is certified that error appears in the above-identified patent and that said Letters Patent is hereby corrected as shown below:

On the Title Page

In Item (72), under "Inventors", in Column 1, Line 2, delete "Zichron Ya'acov (IL)" and insert -- Zikhron Ya'akov (IL) --, therefor.

In the Specification

In Column 7, Line 18, delete "the the" and insert -- the --, therefor.
In Column 7, Line 34, delete "storage 214," and insert -- storage, --, therefor.

In the Claims

In Column 11, Lines 7-8, in Claim 1, delete "ablation parameter data corresponding to the ablation parameter signals;" and insert the same at Line 6, after "and" as a continuation sub-point.

Signed and Sealed this
Twenty-fourth Day of January, 2023

Katherine Kelly Vidal
*Director of the United States Patent and Trademark Office*